US 9,549,661 B2

(12) United States Patent
Raybin et al.

(10) Patent No.: US 9,549,661 B2
(45) Date of Patent: Jan. 24, 2017

(54) MEDICAL DEVICE ACTUATION SYSTEMS AND RELATED METHODS OF USE

(71) Applicant: Boston Scientific Scimed, Inc., Maple Grove, MN (US)

(72) Inventors: Samuel Raybin, Marlborough, MA (US); Naroun Suon, Lawrence, MA (US); Paul Smith, Smithfield, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 162 days.

(21) Appl. No.: 14/192,400

(22) Filed: Feb. 27, 2014

(65) Prior Publication Data

US 2014/0243594 A1    Aug. 28, 2014

Related U.S. Application Data

(60) Provisional application No. 61/770,907, filed on Feb. 28, 2013.

(51) Int. Cl.
*A61B 1/00* (2006.01)
*A61B 1/018* (2006.01)
*A61B 1/04* (2006.01)

(52) U.S. Cl.
CPC ........... *A61B 1/00066* (2013.01); *A61B 1/018* (2013.01)

(58) Field of Classification Search
CPC ............ A61B 1/00128; A61B 1/00133; A61B 1/00121; A61B 1/00137; A61B 1/0014

USPC .......... 600/104, 106, 121, 153, 154
See application file for complete search history.

(56) References Cited

U.S. PATENT DOCUMENTS

| 6,059,719 A * | 5/2000 | Yamamoto ......... A61B 1/00059 600/104 |
| 6,086,530 A * | 7/2000 | Mack ................. A61B 1/00135 600/121 |
| 7,169,167 B2 * | 1/2007 | Chu ....................... A61B 17/29 600/104 |
| 7,371,211 B2 * | 5/2008 | Akiba ............... A61B 17/06066 600/104 |
| 7,727,144 B2 * | 6/2010 | Suzuki ............... A61B 1/00133 600/104 |
| 2009/0171160 A1 * | 7/2009 | Ito ........................ A61B 1/0055 600/141 |

* cited by examiner

*Primary Examiner* — Timothy J Neal
(74) *Attorney, Agent, or Firm* — Bookoff McAndrews, PLLC

(57) ABSTRACT

A medical system including an endoscope having a proximal end, a distal end, and a lumen extending therebetween is disclosed. The endoscope includes a port configured to provide access to the lumen. In addition, the system may include an actuation member slidably disposed through the lumen such that a proximal end of the actuation member extends through the port, and a distal end of the actuation member is operably coupled to an end-effector. The system may further include an actuation handle removably secured to the actuation member. In one embodiment, a portion of the end-effector has dimensions larger than a maximum dimension of the lumen.

14 Claims, 3 Drawing Sheets

MEDICAL DEVICE ACTUATION SYSTEMS AND RELATED METHODS OF USE

CROSS-REFERENCE TO RELATED APPLICATIONS

This application claims the benefit of priority from U.S. Provisional Application No. 61/770,907, filed on Feb. 28, 2013, the entire disclosure of which is incorporated by reference herein.

FIELD OF THE DISCLOSURE

This disclosure relates generally to systems and methods for actuating medical devices. More particularly, embodiments of the present disclosure relate to systems for actuating end-effectors, such as, e.g., end-effectors of minimally invasive tools.

BACKGROUND OF THE DISCLOSURE

Endoscopic and/or laparoscopic devices for use in medical procedures typically are passed through a working channel of a suitable introduction sheath (such as, e.g., an endoscope or laparoscope) positioned in a body cavity in order to reach an operative site at a distal end of the sheath. For purposes of this description, "distal" refers to the end extending into a body and "proximal" refers to the end extending out of the body. The size of an end-effector on the distal end of the endoscopic device, such as, e.g., scissors, snares, forceps, stent delivery devices, biopsy needles, and electro-coagulation probes, therefore, maybe limited by the diameter of the introduction sheath's working channel.

For example, an endoscopic device may include an end-effector, such as, e.g., biopsy forceps, that typically consists of two jaw-like members located distally on an end of a long, flexible tube or sheath. The jaw members are operable to open and close, enabling the jaws to grasp and cut away tissue for biopsy sampling. In at least the closed position, the jaw members must be small enough to fit through the working channel of the endoscope, however, which limits the size of the tissue samples obtained. A 3 French ("Fr.") forceps device that fits in a 7 Fr. ureteroscope acquires tissue samples that are often too small to be accurately evaluated. The size limitation of the jaws also prohibits the use of forceps for other applications, such as grasping gall stones and kidney stones or removing or displacing larger size tissue samples. A working channel of an endoscope that is sized to accommodate an endoscopic device with a larger profile or diameter can inhibit both the flexibility of the endoscope and/or the ability of the endoscope to house other functional components, such as visualization devices, or may increase the outer diameter of the endoscope to an unusable size.

Recent advances in endoscope technology have complicated the task in providing for sufficiently sized end-effectors. On one hand, endoscopes have been reduced in size, responding to the need to navigate through ever smaller bodily cavities. At the same time, endoscopes have become capable of carrying more endoscopic devices, so that endoscopes may be provided with a number of end-effectors, enabling deployment of a range of devices, such as an illumination device, a camera, a tissue resection device, and a tissue retrieval device, all carried in one or more working channels of the same endoscope. The possibility of so many devices being used simultaneously complicates the task of accommodating an oversized end-effector.

Therefore, a need exists for an improved apparatus and method for loading and using an end effector that cannot be inserted completely through the working channel of an endoscope.

SUMMARY

Embodiments of the present disclosure provide a medical system for operating a medical device having an end-effector larger than the working channel of an introduction sheath, such as, e.g., an endoscope.

In one embodiment, the present disclosure provides a medical system. The medical system may include an endoscope having a proximal end, a distal end, and a lumen extending therebetween. The endoscope may further include a port configured to provide access to the lumen. In some embodiments, the port extends along an axis offset from a longitudinal axis of the endoscope, e.g., a Y-connection. The system may further include a support member attached to the port, e.g., removably attached, and a handle received by the support member. In some embodiments, the support member includes a central bore and the handle includes a shank portion that is slidably received within the central bore. The system may be configured to restrict movement (e.g., sliding movement) of the shank relative to the support member, e.g., wherein the central bore of the support member includes a slot (e.g., longitudinal slot) and the shank includes a projection that engages with the slot to restrict movement. The slot may be formed in an inward facing surface of the support member or may extend through a wall of the support member.

In one or more embodiments, the medical system includes an actuation member disposed through the lumen, in a manner that a proximal end of the actuation member extends through the port of the endoscope and a distal end of the actuation member may be operably coupled to an end-effector. The system may include an actuation handle disposed adjacent a portion of the port such that the actuation handle may be configured to be removably secured to the actuation member. The system may include the end-effector with dimensions larger than the maximum dimensions of the lumen. In some embodiments, the system may include a guide ramp at least partially disposed within the lumen for diverting the actuation member into the port. The guide ramp may block the lumen such that the actuation member cannot extend past the guide ramp, e.g., when inserted through the lumen from the distal end of the lumen.

In another embodiment, the present disclosure provides a medical device actuator. The actuator may include an actuation handle having a distal shank removably attached to an actuation member. The actuator may further include a support member having an opening receiving at least a portion of the shank. In addition, a pin radially extending from the shank may engage a slot formed in the support member, limiting the longitudinal and angular movement of the actuation handle. The actuation member may be coupled to the handle through a fastener or linking member, e.g., a set screw, and the fastener may be electrically conductive.

In yet another embodiment, the present disclosure provides a method of preparing a device for a medical procedure, e.g., loading an end-effector into a working channel of an endoscope. The method may include advancing a proximal end of an actuation member operably coupled to an end-effector into a distal end of the channel. The endoscope may include a distal end and a proximal end having a port in communication with the channel. The end-effector may have at least one dimension larger than dimensions of the channel. The method may further include advancing the proximal end of the actuation member through the port of the endoscope and securing the proximal end of the actuation member to an actuator such that the actuator may include a handle portion slidably disposed relative to a fixed portion operably coupled to the port.

Additional objects and advantages of the claimed invention will be set forth in part in the description which follows, and in part will be understood from the description, or may be learned by practice of the embodiments disclosed herein.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Reference will now be made in detail to embodiments of the present disclosure, an example of which is illustrated in the accompanying drawings. Wherever possible, the same reference numbers will be used throughout the drawings to refer to the same or like parts.

As used herein, an "oversized" endoscopic device is one in which the minimum dimensions of an end-effector in a closed or collapsed position exceeds the maximum dimensions of a working channel selected to introduce endoscopic device into a patient's body. Such a device may be referred to an "over-the-scope" device.

Overview

Embodiments of the present disclosure relate to systems and methods for accommodating and employing actuatable end-effectors such as graspers, scissors, dilators, resection devices, biopsy forceps, or similar devices in connection with suitable introduction sheaths, such as, e.g., endoscopes. As is generally known in the art, an endoscope consists of an elongate member, having a distal end, a proximal end, and a lumen extending between the ends. An endoscope handle may be affixed to the proximal end of the endoscope.

The present disclosure describes arrangements in which an endoscopic device includes an end-effector that is too large to fit through the working channel of a conventional introduction sheath. In certain embodiments, for example, a user may insert an actuation member (e.g., a control wire), attached to the end-effector, into the distal end of a selected working channel and advances the actuation member proximally until the end-effector is seated against the distal tip of the endoscope and the proximal end of the actuation member projects through a port on the endoscope handle. An actuation handle may be operably coupled to the proximal end of the actuation member, to control the actuation member as desired. In some instances, the actuation member may take on shape of a wire, a rod, or other similar devices known to those skilled in the art.

In the following sections, embodiments of the present disclosure will be described using an exemplary end-effector—scissors. It will be understood, however, that this choice is merely exemplary and any suitable end-effector known to those skilled in the art may be employed without departing from the scope of the present disclosure.

Exemplary Embodiments

Figure 1:
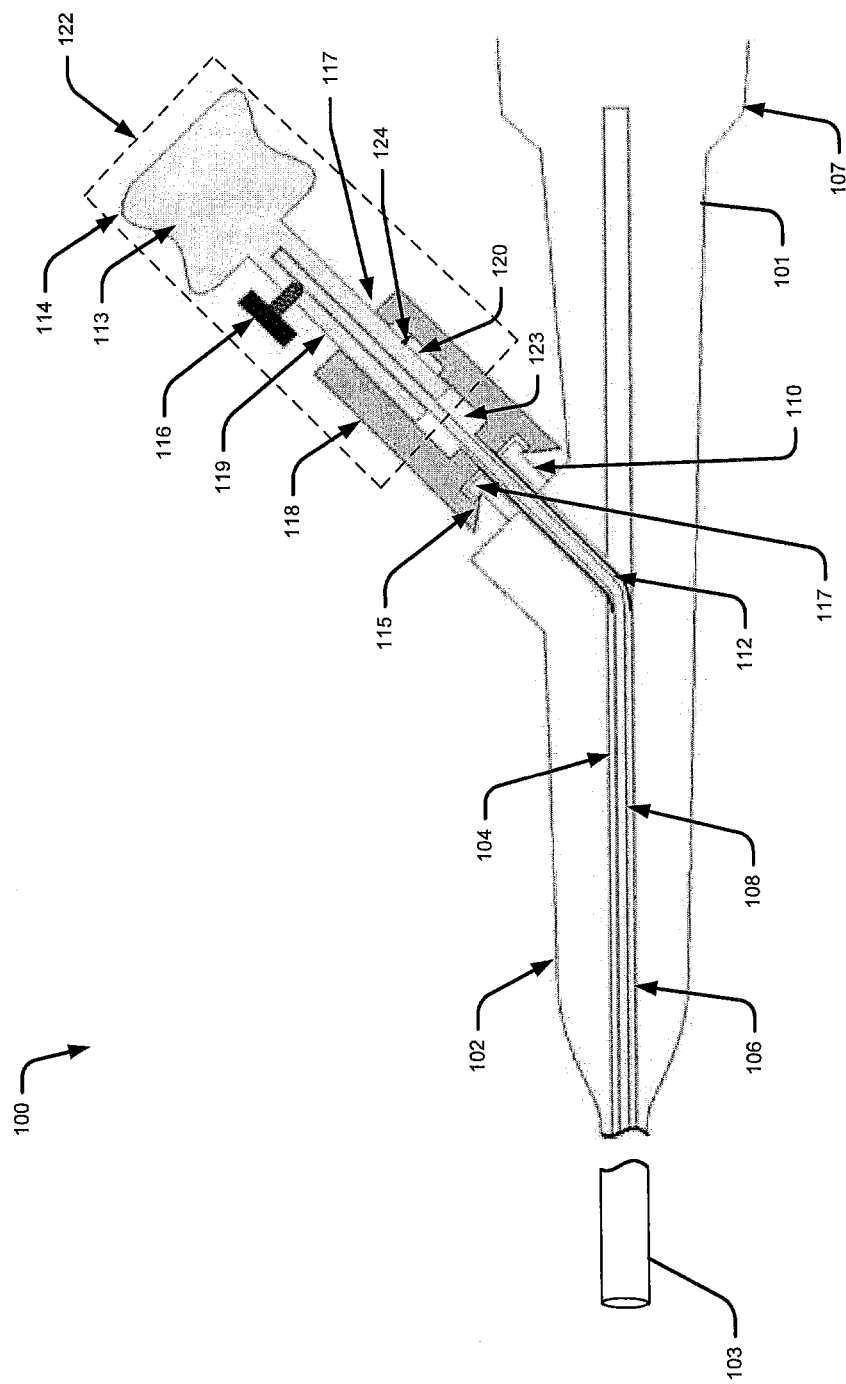
FIG. 1 illustrates a partial sectional view of a system for controlling an over-sized end-effector, according to embodiments of the present disclosure.

FIG. 1 shows a partial sectional view of a system 100 for loading and controlling an end-effector according to embodiments of the present disclosure. The system 100 may include a suitable introduction sheath (not shown), carrying an endoscopic device 102 having a proximal end 101, a distal end 103, lumen 104 extending between the proximal and distal ends 101, 103. The distal end 103 of the endoscopic device 102 may include an end-effector (not shown) extending therefrom, while the proximal end 101 may include a control module 122 extending from a port on the proximal end 101.

Endoscopic device 102 may include an introduction sheath, which may be flexible or rigid, adapted to advance into a body lumen. In general, the endoscopic device 102 may include a tube-like configuration having a circular cross-section. Other cross-sectional shapes may also be contemplated such as elliptical, oval, polygonal, or irregular shapes. In addition, the cross-sectional configuration of the endoscopic device 102 may be uniform along its length or may vary. For instance, the distal end 103 of the endoscopic device 102 may be tapered relative to the proximal end 101, facilitating convenient insertion of the endoscopic device 102 within the body lumen. Moreover, the endoscopic device 102 may be flexible along its entire length or adapted for flexure along portions of its length. Endoscopic device 102 may be any known device or endoscope used for colonoscopy, resectoscopy, cholangioscopy, or mucosal resection, and thus, this device will not be discussed in greater detail.

In an embodiment, the endoscopic device 102 may include a steering mechanism. As is generally known in the art, steering control members may be provided, extending within the lumen or in individual working channels, configured to exert force on the distal end 103, enabling it to flex from side to side while navigating circuitous channels. Other suitable steering mechanisms may include electrical actuators such as, but not limited to, electric wires or the like. Endoscope steering mechanisms are widely known in the art, and any of these mechanisms may be utilized without departing from the scope of the present disclosure.

Endoscopic device 102 may include one or more channels 106, e.g., working channels, through which, the operator may control one or more end-effectors. For example, during a resectomy, the operator may operate a suction end-effector in one channel, and a snare loop end-effector in another channel. Additionally, from time to time during a procedure, the operator may insert a light source, a camera, or other suitable device into another channel 106, which may assist in a medical procedure. Channels 106 extend into the endoscope handle 107, and each channel may be directed by a guide ramp 112 to a port 110 formed in the body of the endoscope handle 107.

The end-effector is discussed in more detail in connection with FIG. 2A, but it will be understood that an actuation member 108, in the form of a wire, rod, or similar device, may extend from the end-effector, through endoscopic device 102, to terminate at a control module 122. Secured to port 110, control module 122 may include, among other things, a support member 118, which may receive the actuation handle 114, which in turn may be operably coupled to actuation member 108. As set out in detail below, control module 122 may provide a stable platform enabling the physician to control the operation of the end-effector.

Actuation member 108 may be made of any suitable material capable of exerting required forces from actuation handle 114 to the end-effector accordingly. In general, the materials employed may include any suitable biocompatible material such as, but not limited to, metals, alloys, polymers or the like either in combination or alone. Exemplary materials may include stainless steel, nitinol, cobalt-chromium alloy, and so forth. The material employed may be sufficiently rigid to ensure that actuation handle movement is appropriately translated to the end-effector. In addition, the actuation member 108 may be sufficiently flexible to maneuver through the endoscopic channels 106. Exemplary actuation member 108 may include a coiled-wire, a braided-wire, or other suitable members known to those in the art. As shown, the actuation member 108 may include a flexible tube-like structure, which may couple to the actuation handle 114 at its proximal end and to the end-effector (not shown) at its distal end.

Support member 118 may be generally cylindrical, with its distal end configured for attachment to port 110 and its proximal end formed to receive actuation handle 114. The attachment mechanism, which in the illustrated embodiment may take the form of flexible barbs 115, may be sized to fit over and engage lip 117 projecting laterally from the inlet of port 110. Alternative structures for the attachment mechanism may include a ring that snaps over the port 110 or a pin extending under it, a hinged clamshell that closes over the port 110 from the side, or any other suitable mechanism known to those in the art. Material suitable for such mechanisms may include a semi-flexible material, which may snap over the port projection. Alternatively, rigid materials, semi-rigid materials, flexible materials, or the like may also be contemplated.

The proximal end of support member 118 may be configured to receive actuation handle 114 into a central bore 123. The central bore 123 opens onto the proximal end of support member 118 and extends distally. In some embodiments, central bore 123 may terminate before reaching the barbs 115, as shown. Additional features associated with central bore 123 are set out below. While FIG. 1 shows the support member 118 including the central bore 123, in other embodiments of the present disclosure, the handle 114 may include a bore configured to receive a projection extending from a support member.

Actuation handle 114 may include a handle portion 113, adapted for manipulation by the physician, and a distally-extending shank 119. Handle portion 113 may be configured as a knob, which may have a fluted circumference and a generally hourglass-shaped longitudinal profile. In some embodiments, knurling may be provided to enhance the physician's grip. Other shapes or surfaces will be apparent to those of skill in the art. Actuation handle 114 may be sized for convenient manipulation by the physician's fingers, or a finger and thumb. Suitable materials for forming actuation handle 114 include polymers and similar conventional materials.

Shank 119 projects distally from the handle portion 113, generally in the form of a cylinder having an internal bore configured to fit over a proximal portion of the actuation member 108. The central bore 123 of support member 118 may be sized to slidably receive shank 119.

The extent of both reciprocal and angular movement of shank 119 within central bore 123, e.g., longitudinal and/or rotational motion, may be further controlled. In FIG. 1, for example, movement of shank 119 within central bore 123 is limited by the cooperative action of a slot 120 formed in the inner wall of central bore 123 and a projection, e.g., pin 124, carried on the exterior surface of shank 119. The skilled artisan will recognize other suitable means of limiting the movement of shank 119 consistent with the present disclosure. As shown in FIG. 1, pin 124 may extend radially from shank 119, and both the length of pin 124 and the depth of slot 120 may be chosen such that pin 124 may move freely within slot 120. Pin 124 may be formed of any material, such as stainless steel. Also, pin 124 may be provided with a spring-loaded compression mechanism (not shown) or other suitable apparatus that allows pin 124 to retract relative to the surface of shank 119, facilitating insertion of shank 119 into central bore 123. In some embodiments, the support member 118 includes more than one piece that may be assembled around pin 124. For example, support member 118 may be assembled from two pieces around pin 124.

Once shank 119 is inserted into central bore 123, pin 124 may extend into and engage the slot 120, the longitudinal movement of actuation handle 114 may be limited by the length of slot 120 and its angular movement may be limited by the width of the slot 120. While FIG. 1 shows slot 120 formed in the inner wall of central bore 123, slot 120 may also pass through the wall of support member 118. In such embodiments, pin 124 may be inserted into slot 120 after shank 119 has been inserted into central bore 123. Further, the shape of slot 120 may be configured to provide a predetermined movement, e.g., rotation and longitudinal movement, of the actuation member 108 and, thus, the end-effector. That is, slot 120 may have a circuitous path that, as the actuation handle 114 is moved longitudinally, affects predetermined rotational movements of the end-effector via one or more cam surfaces.

In some embodiments, the longitudinal and/or angular position of the actuation handle 114 may be detected during operation. Various position detection mechanisms (not shown) may include visual indicators, force feedback, or other mechanisms known to those in the art, all capable of providing linear or rotational position data for actuation handle 114. In some embodiments, indicia formed on the outer surface of support member 118 may provide position indications.

A linking member or fastener, such as, e.g., set screw 116, mounted on shank 119, may operably couple actuation handle 114 to the actuation member 108. In some embodiments, set screw 116 engages a threaded recess in shank 119, thereby clamping actuation member 108 to actuation handle 114. Other suitable fastening devices, such as a pin or a clamp device, as may be known in the art, may be employed as the fastener. In some embodiments, set screw 116 may be adapted for connection to a source of electric power for the end-effector. In such embodiments, set screw 116 is formed of an electroconductive material, such as brass or the like, and an attachment point, such as a threaded portion for accepting a screw device, may be provided in set screw 116. In some embodiments, the electroconductive material could be covered by an insulative material. Such an arrangement would provide a signal or current path from an external source to an end-effector device such as an electro-cautery biopsy forceps.

Thus assembled, actuation handle 114 may move both longitudinally and angularly by pushing, pulling, and rotating actuation member 108 to control the end-effector. In some embodiments, the actuation member 108 may include an electrically conductive material, which may provide electrical energy to an end-effector such as, for example, a cautery device.

Appropriate routing of the actuation member 108 within endoscope handle 107 is provided by guide ramp 112. This element may include a rigid or flexible tube, which may connect the port 110 to channel 106. The diameter of the guide ramp 112 may be smaller than the diameter of the port 110 but greater than the diameter of the actuation member 108, which enables insertion of the actuation member 108 via the port 110. Alternatively, the guide ramp 112 may have a diameter larger than the diameter of the port 110. In certain instances, the two structures may have same diameter, but, the guide ramp 112 may divert the actuation member 108 from the channel 106 into the port 110 instead of continuing proximally up the channel 106.

Figure 2A:
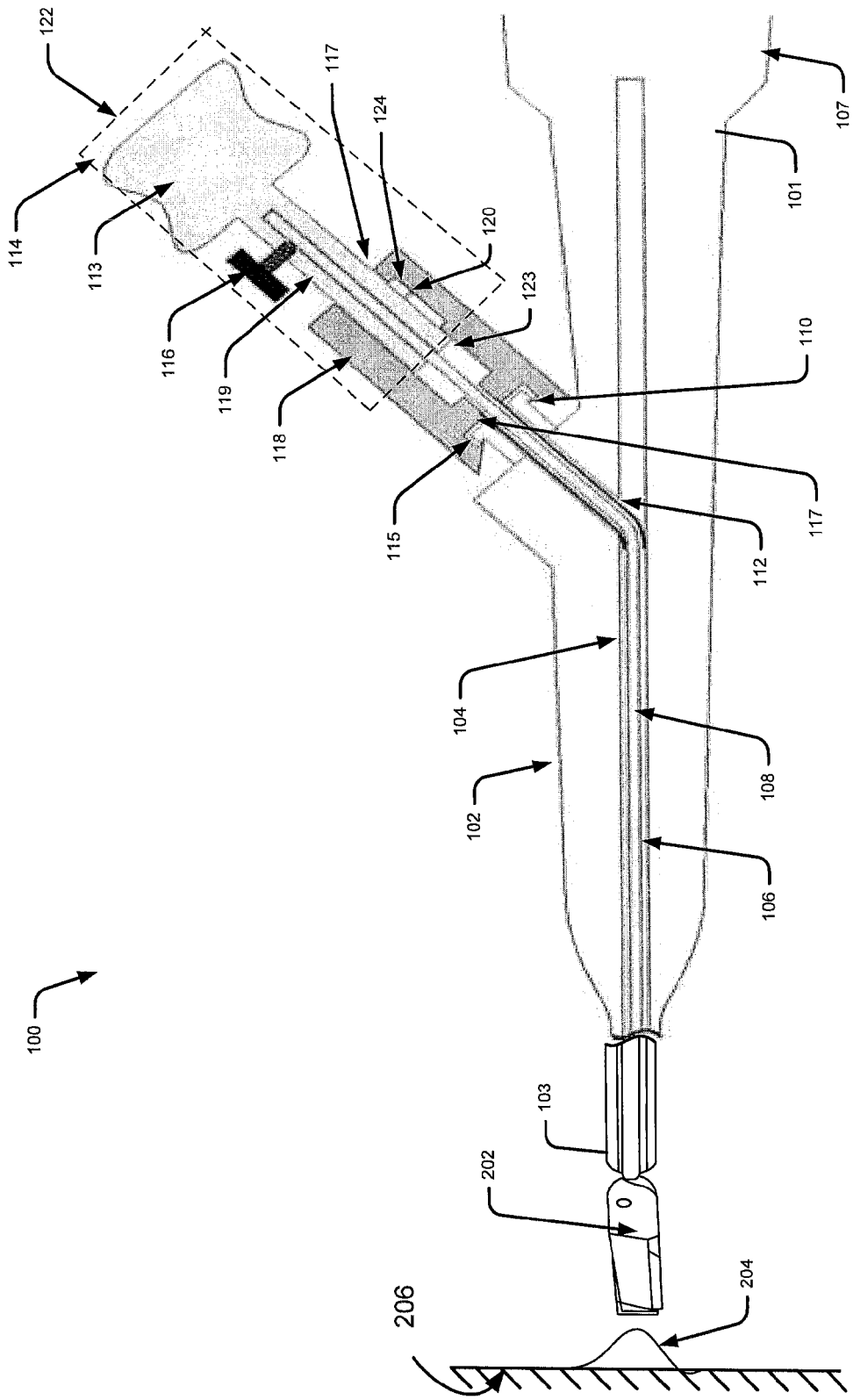
FIGS. 2A and 2B illustrate a method of using the system of FIG. 1, according to embodiments of the present disclosure.
Figure 2B:
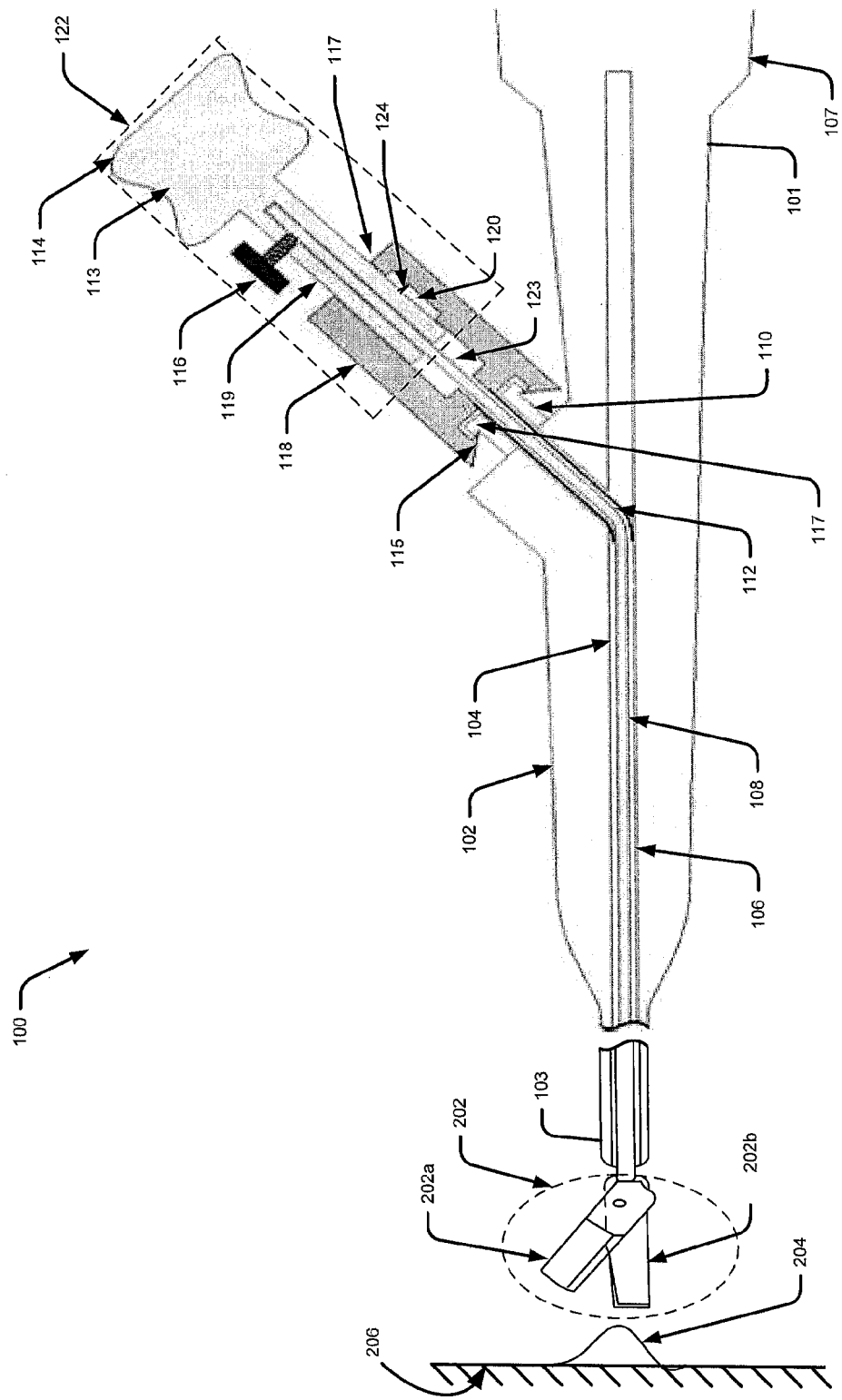

FIGS. 2A and 2B illustrate an exemplary method of using the system 100 to accommodate an oversized end-effector 202 according to the embodiments of the present disclosure. In the illustrated example, the endoscopic device 102, may include an end-effector 202, which may be employed to resect a polyp or lesion 204 or other suspect tissue from the esophageal wall 206 of a patient. Those skilled in the art will appreciate that the apparatus and methods described herein may be used to perform various other medical procedures, including removing suspect tissue from other locations, such as the intestinal wall or other locations.

FIG. 2A illustrates an oversized end-effector 202. As shown, the end-effector takes the form of scissors 202, which may include a pair of jaws 202a and 202b pivotally attached to the actuation member 108 at their proximal end. That arrangement allows the scissors 202 to alternate between open and closed positions. In the closed position, as depicted in FIG. 2A, upper jaw member 202a overlies lower jaw member 202b such that the scissors 202 may distally extend out of the channel 106, while being operably coupled to the actuation member 108. Even in the closed position illustrated in FIG. 2A, the minimum dimension of scissors 202 is greater than the maximum diameter of channel 106. Thus, the conventional method of loading an end-effector from the proximal end of endoscopic device 102 and advancing it distally through the working channel until it exits the distal end of the endoscopic device is not feasible in this configuration.

According to the present disclosure, scissors 202 may be "front loaded," by inserting the proximal end of the attached actuation member 108 into the distal end of channel 106. The actuation member 108 may be advanced through the distal end of endoscopic device 102 and into channel 106 until it reaches the distal end of the endoscopic device 102 and is firmly seated against the distal end of endoscopic device 102. The proximal portion of the actuation member 108 may extend through the endoscopic device through port 110. Actuation member 108 may be operably coupled to the actuation handle 114 as described above.

The length of actuation member 108 may be chosen or trimmed to extend from the proximal end of the scissors 202, through endoscopic device 102 and into handle 114. In the embodiment shown in FIGS. 2A and 2B, a user may attach control module 122 to actuation member 108 by sliding support member 118 over actuation member 108 and advancing the support member 118 until the flexible barbs 115 snap over the lip 117 protruding laterally from port 110. Actuation handle 114 is then fitted over actuation member 108, inserting shank 119 into the central bore 123. Pin 124 may be retracted or depressed to allow it to fit into central bore 123 and then extend to engage slot 120. Set screw 116 connects the actuation handle 114 to actuation member 108. In other embodiments, the support member 118 may be assembled over handle portion 113 with pin 124 in place.

At this point, the endoscopic device 102 and its associated components are prepared for a minimally invasive medical procedure, such as the removal of a lesion 204 on a patient's esophageal wall 206. As shown in FIG. 2A, the physician may introduce the endoscopic device 102 within the esophagus of the patient, effecting that introduction with either a percutaneous incision or a natural opening, such as the mouth. Once inserted, the endoscopic device 102 is directed toward lesion 204 present on esophageal wall 206. A light source and a camera may be inserted in the channel 106 to direct the system 100 to the desired location within the esophagus.

In the open position, as in FIG. 2B, the lower jaw member 202b is separated from the upper jaw member 202a such that the scissors 202 are prepared to perform tissue resection. Jaw members 202a, 202b may be biased to an open position, by spring loading or some other conventional mechanism. Jaw members 202a, 202b may be made of a biocompatible shape memory material such as nitinol.

Next, the distal end 103 of endoscopic device 102 may be advanced to the vicinity of the lesion 204. It should be noted that up to this point, the user has manipulated the endoscope to bring its distal end 103 into position adjacent the target tissue, lesion 204. For the remainder of the process, the operator may directly manipulate scissors 202, using actuation handle 114 to perform the required resection.

Other end-effectors may be used in conjunction with or as an alternative to scissors 202 to accomplish a minimally invasive surgical procedure. In one embodiment, a snare loop (not shown) may extend from one working channel of endoscopic device 102, while a suction device (not shown) advances from another. Using those three tools, the operator could resect lesion 204 using scissors 202, retrieve the resected tissue using the snare loop, and maintain a grip on that tissue as the endoscopic device 102 is removed from the patient's body. Those of skill in the art will understand the variety of end effectors available as well as their optimal use.

Embodiments of the present disclosure may be used to control, manipulate, and steady in any of a wide variety of the end-effector devices known in the art. A number of variations in the constructional details disclosed here is possible without departing from the scope of the present disclosure.

Additionally, alternative embodiments could provide for cooperative control of several end effectors, some or all of which could be oversized. By providing multiple channels 106, several end-effectors and their associated actuation members could terminate either in a single port 110 or in several closely located ports on an endoscopic device 102. Depending on the particular scenario, a single actuation member 108, or multiple actuation members, may be employable to control several end-effectors operating in tandem. As explained above, oversized end-effectors may be frontloaded, and other end effectors that are sized to fit in the provided working channels can be conventionally loaded, i.e., backloaded.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A medical system, comprising:
an endoscope having a proximal end, a distal end, and a lumen extending therebetween, the endoscope further including a port configured to provide access to the lumen;
an actuation member disposed within at least a portion of the lumen, wherein a proximal end of the actuation member extends through the port, a distal end of the actuation member is operably coupled to an end-effector, and the actuation member is uniform from the proximal end of the actuation member to the end-effector, and wherein the end-effector comprises (a) a first jaw moveably coupled directly to the distal end of the actuation member and (b) a second jaw, wherein the end-effector is disposed outside of the distal end of the lumen, and wherein a proximal end of the first jaw and a proximal end of the second jaw remain uncovered by any component of the medical system when the end-effector is in an open configuration, when the end-effector is in a closed configuration, and during insertion of the end-effector within a patient; and
a handle disposed adjacent the port and configured to be removably secured to the actuation member;
wherein at least a portion of the end-effector has a dimension larger than a maximum dimension of the lumen.

2. The system of claim 1, further including a support member removably attached to the port.

3. The system of claim 2, wherein the support member includes an attachment mechanism configured for removable attachment to the port.

4. The system of claim 2, wherein one of the support member and the handle includes a central bore, and the other of the support member and the handle includes a shank portion configured to be slidably received within the central bore.

5. The system of claim 4, wherein the system is configured to restrict movement of the handle relative to the support member.

6. The system of claim 5, wherein the support member includes the central bore and the handle includes the shank portion, the support member further including a slot and the handle further including a projection configured to selectively engage the slot to restrict the movement of the handle relative to the support member.

7. The system of claim 6, wherein the slot is formed in an inward facing surface of the support member.

8. The system of claim 6, wherein the slot extends through a wall of the support member.

9. The system of claim 1, wherein the lumen includes at least one working channel and the port is in communication with the at least one working channel.

10. The system of claim 1, wherein the port extends along an axis offset from a longitudinal axis of the endoscope.

11. The system of claim 1, further including a fastener to removably secure the handle to the actuation member.

12. The system of claim 11, wherein the fastener is electrically conductive.

13. The system of claim 1, further including a guide ramp at least partially disposed within the lumen for diverting the actuation member into the port.

14. The system of claim 13, wherein the guide ramp blocks the lumen such that the actuation member cannot extend past the guide ramp.

* * * * *